United States Patent
Behnke, II et al.

(10) Patent No.: US 9,254,172 B2
(45) Date of Patent: *Feb. 9, 2016

(54) SHIELDING FOR AN ISOLATION APPARATUS USED IN A MICROWAVE GENERATOR

(71) Applicant: Covidien LP, Mansfield, MA (US)

(72) Inventors: Robert J. Behnke, II, Erie, CO (US); Tom E. McMunigal, Mead, CO (US)

(73) Assignee: Covidien LP, Mansfield, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 13/793,583

(22) Filed: Mar. 11, 2013

(65) Prior Publication Data

US 2013/0190750 A1    Jul. 25, 2013

Related U.S. Application Data

(63) Continuation of application No. 12/203,734, filed on Sep. 3, 2008, now Pat. No. 8,403,924.

(51) Int. Cl.
  *A61B 18/04*    (2006.01)
  *A61B 18/18*    (2006.01)
  *A61N 5/02*    (2006.01)

(52) U.S. Cl.
  CPC .............. *A61B 18/1815* (2013.01); *A61B 18/18* (2013.01); *A61N 5/02* (2013.01)

(58) Field of Classification Search
  USPC ................... 606/32–34, 45–47; 330/136, 313
  See application file for complete search history.

(56) References Cited

U.S. PATENT DOCUMENTS

| | | |
|---|---|---|
| 3,631,363 A | 12/1971 | Miller |
| 3,908,176 A | 9/1975 | De Boer et al. |
| 4,229,714 A | 10/1980 | Yu |
| 4,397,313 A | 8/1983 | Vaguine |
| 4,462,412 A | 7/1984 | Turner |
| 4,572,190 A | 2/1986 | Azam et al. |
| 4,798,215 A | 1/1989 | Turner |
| 5,097,844 A | 3/1992 | Turner |
| 5,097,846 A | 3/1992 | Larsen |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

Anonymous. (1999) Auto Suture MIBB Site Marker: Single Use Clip Applier, United States Surgical (Product instructions), 2 pages.

(Continued)

*Primary Examiner* — Nicholas Lucchesi
*Assistant Examiner* — Anh Bui

(57) ABSTRACT

A system for reducing radiated emissions the system including a microwave generator that supplies microwave energy at a fundamental frequency, a coaxial transmission cable that transmits microwave energy between the microwave generator and a microwave energy delivery device and an isolation apparatus connected between the microwave generator and the coaxial transmission cable. The isolation apparatus is configured to electrically isolate the coaxial transmission cable from the microwave generator and capacitively couple the microwave generator ground to the coaxial transmission cable.

9 Claims, 5 Drawing Sheets

(56) References Cited

U.S. PATENT DOCUMENTS

| | | | |
|---|---|---|---|
| 5,275,597 | A | 1/1994 | Higgins et al. |
| 5,405,346 | A | 4/1995 | Grundy et al. |
| 5,417,210 | A | 5/1995 | Funda et al. |
| 5,562,720 | A | 10/1996 | Stern et al. |
| 5,683,382 | A | 11/1997 | Lenihan et al. |
| 5,693,082 | A * | 12/1997 | Warner et al. .................. 607/156 |
| 5,865,788 | A | 2/1999 | Edwards et al. |
| 5,904,709 | A | 5/1999 | Arndt et al. |
| 5,931,836 | A | 8/1999 | Hatta et al. |
| 5,957,969 | A | 9/1999 | Warner et al. |
| 5,961,871 | A | 10/1999 | Bible et al. |
| 5,983,141 | A | 11/1999 | Sluijter et al. |
| 6,016,452 | A | 1/2000 | Kasevich |
| 6,031,375 | A | 2/2000 | Atalar et al. |
| 6,067,475 | A | 5/2000 | Graves et al. |
| 6,097,985 | A | 8/2000 | Kasevich et al. |
| 6,134,476 | A | 10/2000 | Arndt et al. |
| 6,175,768 | B1 | 1/2001 | Arndt et al. |
| 6,181,970 | B1 | 1/2001 | Kasevich |
| 6,216,704 | B1 | 4/2001 | Ingle et al. |
| 6,228,079 | B1 | 5/2001 | Koenig |
| 6,233,490 | B1 | 5/2001 | Kasevich |
| 6,246,912 | B1 | 6/2001 | Sluijter et al. |
| 6,273,886 | B1 | 8/2001 | Edwards et al. |
| 6,293,941 | B1 | 9/2001 | Strul et al. |
| 6,358,245 | B1 | 3/2002 | Edwards et al. |
| 6,375,606 | B1 | 4/2002 | Garibaldi et al. |
| 6,451,015 | B1 | 9/2002 | Rittman, III et al. |
| 6,471,696 | B1 | 10/2002 | Berube et al. |
| 6,485,486 | B1 | 11/2002 | Trembly et al. |
| 6,603,994 | B2 | 8/2003 | Wallace et al. |
| 6,699,241 | B2 | 3/2004 | Rappaport et al. |
| 6,706,040 | B2 | 3/2004 | Mahon et al. |
| 6,725,080 | B2 | 4/2004 | Melkent et al. |
| 6,743,225 | B2 | 6/2004 | Sanchez et al. |
| 6,778,044 | B2 | 8/2004 | Fehrenbach et al. |
| 6,784,405 | B2 | 8/2004 | Flugstad et al. |
| 6,847,848 | B2 | 1/2005 | Sterzer et al. |
| 7,200,010 | B2 | 4/2007 | Broman et al. |
| 7,226,446 | B1 | 6/2007 | Mody et al. |
| 7,344,533 | B2 | 3/2008 | Pearson et al. |
| 7,393,352 | B2 | 7/2008 | Berube |
| 7,419,487 | B2 | 9/2008 | Johnson et al. |
| 7,439,736 | B2 | 10/2008 | Meaney et al. |
| 7,467,015 | B2 | 12/2008 | van der Weide |
| 7,565,207 | B2 | 7/2009 | Turner et al. |
| 7,642,451 | B2 | 1/2010 | Bonn |
| 7,875,024 | B2 | 1/2011 | Turovskiy et al. |
| 8,035,570 | B2 | 10/2011 | Prakash et al. |
| 8,059,059 | B2 | 11/2011 | Bonn |
| 8,118,808 | B2 | 2/2012 | Smith et al. |
| 8,152,802 | B2 | 4/2012 | Podhajsky et al. |
| 8,162,932 | B2 | 4/2012 | Podhajsky et al. |
| 8,167,875 | B2 | 5/2012 | Podhajsky et al. |
| 8,174,267 | B2 | 5/2012 | Brannan et al. |
| 8,180,433 | B2 | 5/2012 | Brannan et al. |
| 8,182,480 | B2 | 5/2012 | Huseman |
| 8,192,427 | B2 | 6/2012 | Buysse |
| 8,197,473 | B2 | 6/2012 | Rossetto et al. |
| 8,202,270 | B2 | 6/2012 | Rossetto et al. |
| 8,211,098 | B2 | 7/2012 | Paulus |
| 8,211,099 | B2 | 7/2012 | Buysse et al. |
| 8,211,100 | B2 | 7/2012 | Podhajsky et al. |
| 8,216,227 | B2 | 7/2012 | Podhajsky |
| 8,221,418 | B2 | 7/2012 | Prakash et al. |
| 8,226,639 | B2 | 7/2012 | Podhajsky et al. |
| 8,235,981 | B2 | 8/2012 | Prakash et al. |
| 8,242,782 | B2 | 8/2012 | Brannan et al. |
| 8,246,614 | B2 | 8/2012 | DeCarlo |
| 8,248,075 | B2 | 8/2012 | Brannan et al. |
| 8,251,987 | B2 | 8/2012 | Willyard |
| 8,257,349 | B2 | 9/2012 | Orszulak |
| 8,262,703 | B2 | 9/2012 | Prakash et al. |
| 8,287,527 | B2 | 10/2012 | Brannan et al. |
| 8,287,528 | B2 | 10/2012 | Wham et al. |
| 8,287,529 | B2 | 10/2012 | Orszulak |
| 8,292,880 | B2 | 10/2012 | Prakash et al. |
| 8,292,881 | B2 | 10/2012 | Brannan et al. |
| 8,333,759 | B2 | 12/2012 | Podhajsky |
| 8,343,149 | B2 | 1/2013 | Rossetto et al. |
| 8,346,370 | B2 | 1/2013 | Haley et al. |
| 8,353,902 | B2 | 1/2013 | Prakash |
| 8,353,903 | B2 | 1/2013 | Podhajsky |
| 8,377,053 | B2 | 2/2013 | Orszulak |
| 8,382,750 | B2 | 2/2013 | Brannan |
| 8,394,086 | B2 | 3/2013 | Behnke et al. |
| 8,394,087 | B2 | 3/2013 | Willyard et al. |
| 8,394,092 | B2 | 3/2013 | Brannan |
| 8,403,924 | B2 | 3/2013 | Behnke et al. |
| 8,409,186 | B2 | 4/2013 | Behnke et al. |
| 8,435,237 | B2 | 5/2013 | Bahney |
| 8,463,396 | B2 | 6/2013 | Podhajsky |
| 8,512,328 | B2 | 8/2013 | Rossetto et al. |
| 8,734,444 | B2 | 5/2014 | Kerr |
| 8,834,409 | B2 | 9/2014 | Manley |
| 8,834,460 | B2 | 9/2014 | Peterson |
| 8,852,179 | B2 | 10/2014 | Ward et al. |
| 8,945,111 | B2 | 2/2015 | Brannan et al. |
| 2002/0022836 | A1 | 2/2002 | Goble et al. |
| 2002/0087151 | A1 | 7/2002 | Mody et al. |
| 2003/0032951 | A1 | 2/2003 | Rittman et al. |
| 2004/0097805 | A1 | 5/2004 | Verard et al. |
| 2004/0242992 | A1 | 12/2004 | Hareyama |
| 2005/0033278 | A1 | 2/2005 | McClurken et al. |
| 2005/0101947 | A1 | 5/2005 | Jarrard et al. |
| 2006/0030914 | A1 | 2/2006 | Eggers et al. |
| 2006/0224152 | A1 | 10/2006 | Behnke et al. |
| 2007/0203480 | A1 | 8/2007 | Mody et al. |
| 2007/0233057 | A1 | 10/2007 | Konishi |
| 2007/0282319 | A1 | 12/2007 | van der Weide et al. |
| 2009/0018536 | A1 | 1/2009 | Behnke |
| 2009/0222002 | A1 | 9/2009 | Bonn et al. |
| 2009/0248005 | A1 | 10/2009 | Rusin et al. |
| 2009/0248006 | A1 | 10/2009 | Paulus et al. |
| 2009/0254077 | A1 | 10/2009 | Craig |
| 2009/0306652 | A1 | 12/2009 | Buysse et al. |
| 2010/0030206 | A1 | 2/2010 | Brannan et al. |
| 2010/0030210 | A1 | 2/2010 | Paulus |
| 2010/0045558 | A1 | 2/2010 | Rossetto |
| 2010/0045559 | A1 | 2/2010 | Rossetto |
| 2010/0076422 | A1 | 3/2010 | Podhajsky |
| 2010/0082083 | A1 | 4/2010 | Brannan et al. |
| 2010/0087808 | A1 | 4/2010 | Paulus |
| 2010/0094273 | A1 | 4/2010 | Rossetto et al. |
| 2010/0097284 | A1 | 4/2010 | Brannan et al. |
| 2010/0256624 | A1 | 10/2010 | Brannan et al. |
| 2010/0262134 | A1 | 10/2010 | Jensen et al. |
| 2011/0071582 | A1 | 3/2011 | Willyard et al. |
| 2011/0118721 | A1 | 5/2011 | Brannan |
| 2011/0208179 | A1 | 8/2011 | Prakash et al. |

FOREIGN PATENT DOCUMENTS

| | | |
|---|---|---|
| DE | 1099658 B | 2/1961 |
| DE | 1099858 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 24398587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |

(56) References Cited

FOREIGN PATENT DOCUMENTS

| | | |
|---|---|---|
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4206433 A1 | 9/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 267403 A2 | 5/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 481 685 A1 | 4/1992 |
| EP | 0 521 264 A2 | 1/1993 |
| EP | 0 556 705 A1 | 8/1993 |
| EP | 0 558 429 A1 | 9/1993 |
| EP | 0572131 A1 | 12/1993 |
| EP | 608609 A2 | 8/1994 |
| EP | 0541930 B1 | 3/1998 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1 159 926 A2 | 12/2001 |
| EP | 1278007 | 1/2003 |
| EP | 1186274 | 4/2006 |
| EP | 1 810 627 A1 | 7/2007 |
| EP | 1810630 A1 | 7/2007 |
| EP | 2319412 A1 | 5/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2364461 A | 4/1978 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 607850 A | 9/1948 |
| GB | 702510 A | 1/1954 |
| GB | 855459 A | 11/1960 |
| GB | 902775 A | 8/1962 |
| GB | 2164473 A | 3/1986 |
| GB | 2214430 A | 9/1989 |
| GB | 2358934 A | 8/2001 |
| JP | 6-502328 | 3/1992 |
| JP | 5-5106 | 1/1993 |
| JP | 05-40112 | 2/1993 |
| JP | 06343644 A | 12/1994 |
| JP | 06343644 A | 12/1994 |
| JP | 07265328 A | 10/1995 |
| JP | 08056955 A | 3/1996 |
| JP | 8-56955 | 5/1996 |
| JP | 08252263 A | 10/1996 |
| JP | 08252263 A | 10/1996 |
| JP | 9-10223 C | 1/1997 |
| JP | 09010223 A | 1/1997 |
| JP | 11244298 A | 9/1999 |
| JP | 11244298 A | 9/1999 |
| JP | 2000342599 A | 12/2000 |
| JP | 2000342599 A | 12/2000 |
| JP | 2000350732 A | 12/2000 |
| JP | 2000350732 A | 12/2000 |
| JP | 2001008944 A | 1/2001 |
| JP | 2001008944 A | 1/2001 |
| JP | 2001029356 A | 2/2001 |
| JP | 2001029356 A | 2/2001 |
| JP | 2001128990 A | 5/2001 |
| JP | 2001128990 A | 5/2001 |
| SU | 166452 | 11/1964 |
| SU | 401367 A1 | 10/1973 |
| SU | 727201 A2 | 4/1980 |
| WO | 97/41924 A1 | 11/1997 |
| WO | 97/43971 A2 | 11/1997 |
| WO | WO-97/41924 A1 | 11/1997 |
| WO | WO-97/43971 A2 | 11/1997 |
| WO | 00/48672 A1 | 8/2000 |
| WO | WO-00/48672 A1 | 8/2000 |
| WO | 00/51513 A1 | 9/2000 |
| WO | WO-00/51513 A1 | 9/2000 |
| WO | 01/01847 | 1/2001 |
| WO | WO-01/01847 | 1/2001 |
| WO | 01/74252 A2 | 10/2001 |
| WO | WO-01/74252 A2 | 10/2001 |
| WO | 02/45790 A2 | 6/2002 |
| WO | WO-02/45790 A2 | 6/2002 |
| WO | 02/061880 A2 | 8/2002 |
| WO | WO-02/061880 A2 | 8/2002 |
| WO | 03/047043 A1 | 6/2003 |
| WO | WO-/03/047043 A1 | 6/2003 |
| WO | 2004112628 A1 | 12/2004 |
| WO | WO-2004/112628 A1 | 12/2004 |
| WO | 2005/016119 A2 | 2/2005 |
| WO | WO-2005/016119 A2 | 2/2005 |
| WO | WO-2006/105121 A2 | 10/2006 |
| WO | 2007/076924 A2 | 7/2007 |
| WO | WO-2007/076924 A2 | 7/2007 |

OTHER PUBLICATIONS

Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/ Wire Localizer, Namic® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991) pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

(56) References Cited

OTHER PUBLICATIONS

C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surge" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-inputcom/lightkey> 2002.
Esterline Product Literature, "Light Key: Visualize a Virtual Keyboard. One With No Moving Parts", Nov. 1, 2003; 4 pages.
Goldberg et al., "Image-guided Radiofrequency Tumor Ablation: Challenges and Opportunities—Part I", (2001) J Vasc. Interv. Radiol, vol. 12, pp. 1021-1032.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MEDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Murakami, R. et al., (1995). "Treatment of Hepatocellular Carcinoma: Value of Percutaneous Microwave Coagulation," American Journal of Radiology (AJR) 164:1159-1164.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 11/242,458 dated Oct. 3, 2005 inventor: Becker.
U.S. Appl. No. 08/483,742, filed Jun. 7, 1995.
U.S. Appl. No. 08/136,098, filed Oct. 14, 1993.
U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hernicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991: pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridum Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83: (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2:(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahi et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1990.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.

(56) References Cited

OTHER PUBLICATIONS

International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP09169377.0 dated Dec. 15, 2009.
H. Schwarzmaler et al., "Magnetic Resonance Imaging of Microwave Induced Tissue Heating" Dept. of Laser Medicine & Dept. of Diagnostic Radiology; Heinrich-Heine-University, Duesseldorf, Germany: Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP09169376.2 dated Dec. 16, 2009.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/243,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1987) Horner Mammalok™ Breast Lesion Needle/Wire Localizer, Namic® Anglographic Systems Divison, Glens Falls, New York, (Hospital produts price list), 4 pages.
Anonymous. Blunt Tubes with Finished Ends. Pointed Cannula, Popper & Sons Biomedical Instrument Divison, (Products Price List), one page, Jul. 19, 2000.
B.T. Heniford M.D. et al., "Initial Research and Clinical Results with an Electrothermal Bipolar Vessel Sealer" Oct. 1999.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advaned Surgery Program, Carolinas Medical Center,Charlotte, NC 2003.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw.cndot.Hill, vol. 111, (1984), pp. 2490-2499.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Velnous Complex" Sales/Produt Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Goldberg et al., "Image-guided Radiofrequency Tumor Ablation: Challenges and Opportunities—Part I", (2001) J Vasc. Interv. Radiol. vol. 12, pp. 1021-1032.
Herman at al., "Laparoscopic Intestinal Resection With the LigaSure. TM. Vessel Sealing System: A Case Report" Innovations That Work, Feb. 2002.
Jarrett et al., "Use of the LigaSure.TM. Vessel Sealing System for Peri-Hllar Vessels in Laparoscopic Nephrectomy" Sales/Product Literature 2000.
Johnson, "Evaluation of the LigaSure.TM. Vessel Sealing System in Hemorrhoidectomy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1993.
Joseph Ortenberg, "LigaSure.TM. System Used in Laparoscopic 1st and 2nd Stage Orchiopexy" Innovations That Work, Nov. 2002.

(56) References Cited

OTHER PUBLICATIONS

K. Ogata, Modern Control Engineering, Prentice-Hall, Englewood Cliffs, N.J., 1970.
Kopans, D.B. et al., (Nov. 1985) "Spring Hookwire Breast Lesion Localizer: Use with Rigid-Compression. Mammographic Systems," Radiology 157(2):537-528.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
M. A. Astrahan, "A Localized Current Field Hyperthermia System for Use with 192-Iridium Interstitial Implants" Medical Physics. 9(3), May/Jun. 1982.
McGahan et al., (1995) "Percutaneous Ultrasound-guided Radiofrequency Electroautery Ablation of Prostate Tissue in Dogs", Acad Radiol, vol. 2, No. 1: pp. 61-65.
MDTECH product literature (Mar. 2000) I'D Wire: product description, 1 page.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Ni Wei et al., "A Signal Processing Method for the Coriolis Mass Flowmeter Based on a Normalized . . . " Journal of Applied Sciences—Yingyong Kexue Xuebab, Shanha CN, vol. 23, No. 2:(Mar. 2005); pp. 160-184.
Organ, L. W., "Eletrophysiologic Principles of Radiofrequency Lesion Making" Appl. Neurophysiol, vol. 39: pp. 69-76 (1976/77).
Palazzo et al., "Randomized clinical trial of LigaSure.TM. versus open Haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrholdectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sylvain Labonte et al., "Monopole Antennas for Microwave Cathether Ablation", IEEE Trans. on Microwave Theory and Techniques, vol. 44, No. 10, pp. 1832-1840, Oct. 1995.
S. Humphries Jr. et al., "Finite.cndot.Element Codes to Model Electrical Heating and Non.cndot.Linear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.comlmedicalUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
W. Scott Helton, "LigaSure.TM. Vessel Sealing System: Revolutionary Hemostasis Product for General Surgery" Sales/Product Literature 1999.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2004.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2008.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2008.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2004.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.

(56) References Cited

OTHER PUBLICATIONS

European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37111 dated Jul. 28, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.

* cited by examiner

SHIELDING FOR AN ISOLATION APPARATUS USED IN A MICROWAVE GENERATOR

CROSS-REFERENCE TO RELATED APPLICATION

This application is a Continuation of U.S. patent application Ser. No. 12/203,734 filed on Sep. 3, 2008, the entire contents of which are incorporated by reference herein for all purposes.

BACKGROUND

1. Technical Field

The present disclosure relates to systems and methods for performing a medical procedure, wherein the medical procedure includes the generation and safe transfer of energy from an energy source to a microwave energy delivery device. More particularly, a microwave energy delivery system including an isolation apparatus is disclosed to reduce undesirable radiated emissions during the delivery of microwave energy.

2. Background of Related Art

Microwave delivery systems and ablation procedures using microwave energy are designed to safely deliver microwave energy to a target tissue. The equipment, the act of energy delivery or the procedures used to deliver energy may be regulated by various governmental or industrial regulations or standards, such as, for example, FCC regulations and standards for microwave equipment or electromagnetic compatibility (EMC) regulations and standards to ensure that the microwave equipment does not interfere with other electronic equipment. Industrial standards may be related to patient safety, such as, for example, providing sufficient electrical isolation between a generator and a patient. As such, the microwave energy generation and transmission devices are specifically designed to minimize and reduce undesirable energy delivery.

One common design practice used to ensure patient safety in electrosurgical generators is to create an isolation barrier between the generator and the patient. This is accomplished by isolating the generator output from an earth ground. Isolation barriers may be created by various generally accepted circuits, such as, for example, a transformer or capacitors that would have a low impedance at about 60 Hz. While the practice of including an isolation barrier is generally effective with systems delivering energy in RF frequencies, delivering energy with a signal in a microwave frequency provides new opportunities for microwave generator and system designers.

One such opportunity for microwave generators and their system designers is that microwave generators need to pass FCC regulations for EMC while operating. The fundamental frequency (i.e., the frequency band of the desirable microwave signal) is usually in an Instrumental Scientific Medical (ISM) band and is not an issue. Instead, EMC issues typically evolve around unintended energy discharges at frequencies outside of the IMS band, such as, for example, harmonics frequencies of the fundamental frequency above the ISM band.

Harmonics of the fundamental frequency may be a product of the microwave generator's signal generator or may be induced at various locations in the microwave generator circuits and/or the microwave energy delivery circuit. For example, harmonics are sometimes a product of the isolation barrier that is intended to isolate the generator from the patient and to provide patient safety. For example, the isolation barrier in a microwave delivery system may include the floating of the coaxial shield (i.e., the practice of not attaching the coaxial shield to the ground of the generator). Microwave energy may run along the shield of the coaxial cable and cause the coax cable to radiate as an antenna. This antenna affect can cause the generator's harmonics to be amplified and fail one or more EMC standards.

The present disclosure describes a system including an isolation apparatus to reduce undesirable EMC during the delivery of microwave energy.

SUMMARY

The present disclosure relates generally to a system and isolation apparatus for reducing undesirable radiated emissions during a medical procedure. More particularly, in one embodiment of the present disclosure a system includes a microwave generator that supplies microwave energy at a fundamental frequency, a coaxial transmission cable that transmits microwave energy between the microwave generator and a microwave energy delivery device and an isolation apparatus connected between the microwave generator and the coaxial transmission cable. The isolation apparatus is configured to electrically isolate the coaxial transmission cable from the microwave generator and capacitively couple the microwave generator ground to the coaxial transmission cable.

The isolation apparatus may further include an isolation circuit board configured to electrically isolate the microwave generator and the coaxial transmission cable while passing microwave energy therebetween. In one embodiment a ground reference shield may be connected to a microwave generator ground reference and configured to house the isolation circuit board. In another embodiment an isolation barrier may be positioned between the ground reference shield and the patient reference shield.

In yet another embodiment the ground reference shield and the patient reference shield may form a capacitor and capacitively couple the microwave generator ground reference to the coaxial transmission cable. The capacitive coupling between the ground reference shield and the patient reference shield may be adjustable. By varying the overlapping surface area between the ground reference shield and the patient reference shield, the gap between the overlapping portions of the ground reference shield and the patient reference shield or a dielectric property of the isolation barrier.

In still another embodiment according to the present disclosure, an isolation apparatus includes an isolation circuit board with an isolation circuit and a shield coupling that provides isolation between a microwave generator and a coaxial transmission cable. The isolation circuit capacitively couples a microwave generator and a coaxial transmission cable. The isolation circuit board passes energy at a fundamental frequency between the microwave generator and the coaxial transmission cable. The shield coupling includes a ground reference shield connected to a ground reference of the microwave generator and a patient reference shield connected to the outer sheath of the coaxial transmission cable. The shield coupling is configured to house the isolation circuit board. The ground reference shield and the patient reference shield are capacitively coupled and form a shield coupling capacitor. The shield coupling capacitor provides a ground reference for the coaxial transmission cable.

In yet another embodiment, the isolation apparatus may include an isolation barrier between the ground reference shield and the patient reference shield. The capacitive coupling between the ground reference shield and the patient reference shield may be adjustable by varying the overlapping surface area between the ground reference shield and the patient reference shield, the gap between the overlapping portions of the ground reference shield and the patient reference shield, or a dielectric property of the isolation barrier.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
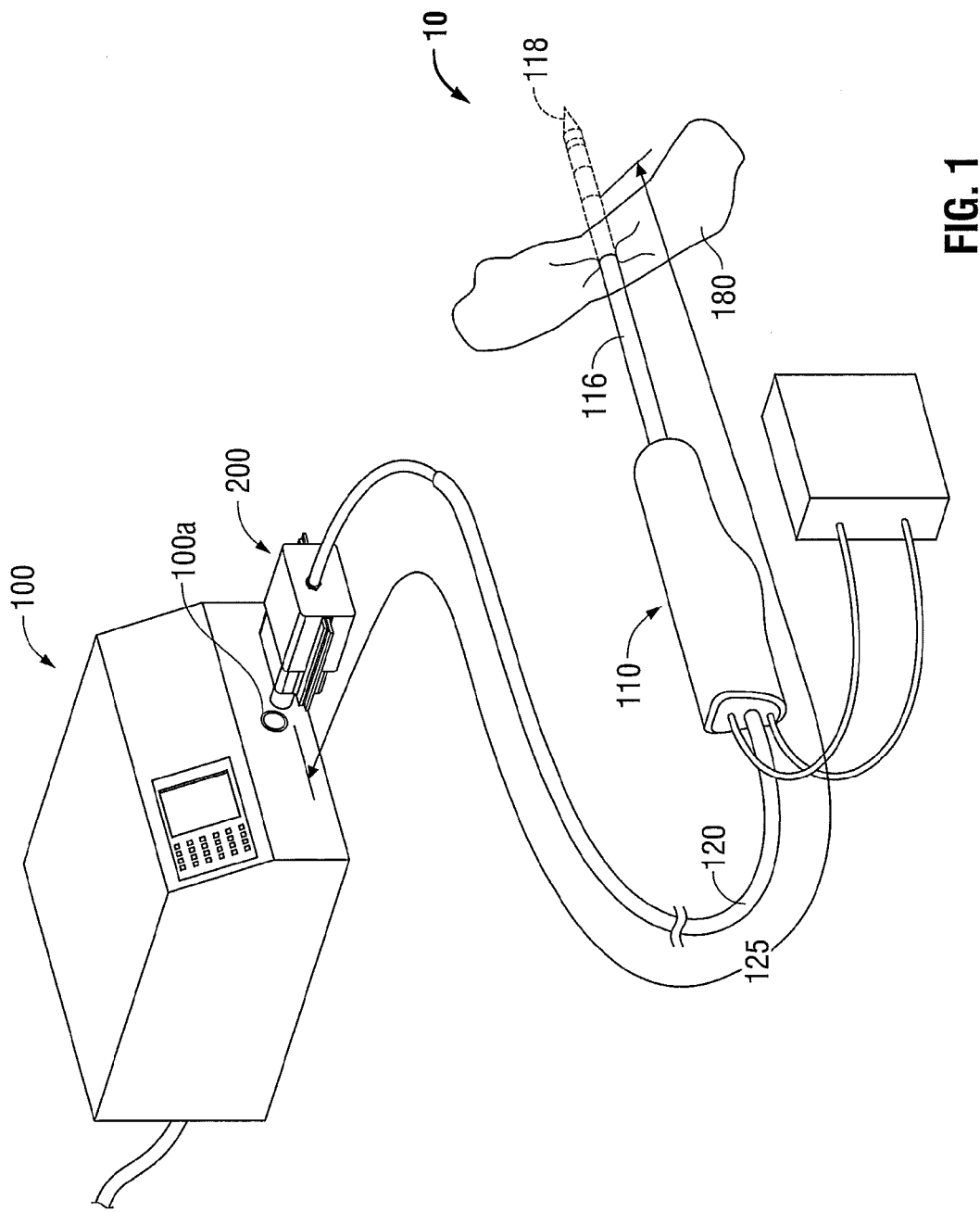
FIG. 1 is a functional block diagram of a microwave energy delivery including an isolation apparatus according to an embodiment of the present disclosure.

Referring to FIG. 1, a microwave energy delivery system including a microwave generator 100, a microwave energy delivery device 110, a coaxial transmission cable 120 and an isolation apparatus 200 employing embodiments of the present disclosure, is referenced generally as microwave delivery system as 10. The isolation apparatus 200 is connected between the microwave generator 100 and the microwave energy delivery device 110. In one embodiment of the present disclosure the isolation apparatus 200 connects to the coaxial connector 100a of the microwave generator 100 and the coaxial transmission cable 120. Isolation apparatus 200 may also be placed at various other positions in the microwave energy transmission circuit.

Microwave energy delivery device 110 includes coaxial transmission cable 120 (i.e., a coaxial transmission cable portion 120 is permanently affixed to the microwave energy delivery device 110), as illustrated in FIG. 1. Alternatively, coaxial transmission cable 120 may be separate from the microwave energy delivery device 110 and the isolation apparatus 200. In yet another embodiment, isolation apparatus 200 may include a coaxial transmission cable portion (not shown).

In yet another embodiment, the microwave energy transmission path 125 includes the transmission path of the isolation apparatus 200, the coaxial transmission cable 120 and the handle 116 (the transmission portion of the microwave energy delivery apparatus 110 proximal the antenna 118). The length of the microwave energy transmission path 125 is related to at least one parameter of the fundamental frequency of the energy generated by the microwave generator 100.

As illustrated in FIG. 1, microwave energy delivery device includes a percutaneous device having a sharpened tip configured to penetrate tissue. Isolation apparatus 200 may also be used with a catheter insertable microwave energy delivery device, a skin surface treatment microwave energy delivery device and a deployable microwave energy delivery device or other suitable device configured to delivery microwave energy to tissue 180.

Figure 2A:
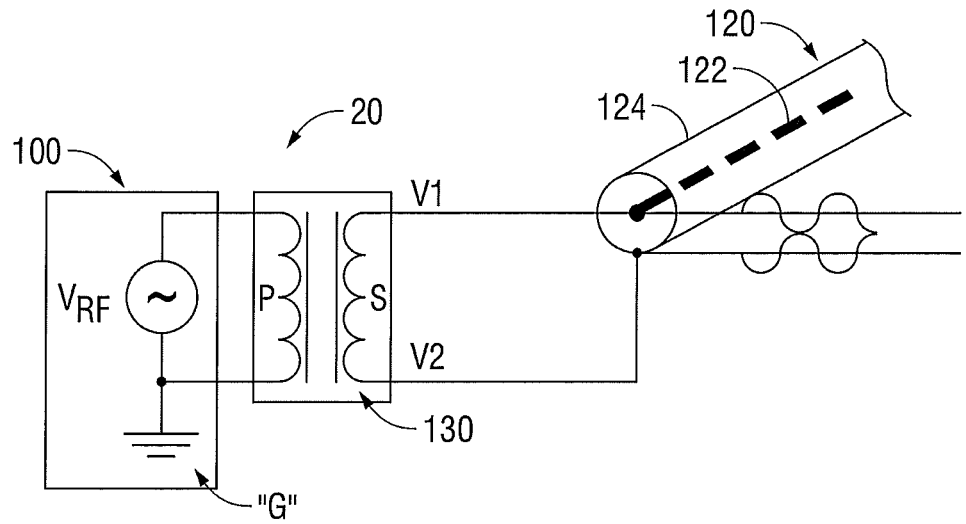
FIG. 2A is an electrical schematic of a conventional microwave energy delivery circuit.

FIG. 2A is an electrical schematic of a conventional microwave energy delivery circuit 20 without an isolation apparatus of the present disclosure. The circuit 20 includes a microwave energy source "VRF", a generator isolation device 130 (i.e., a transformer), and an electrical load 120 (i.e., a coaxial transmission cable 120 connected to a microwave energy delivery device (not shown)). In FIG. 2A, and as described herein, transformer 130 is shown merely as an example of a suitable generator isolation device. Generator isolation device 130 may be any suitable device that transfers energy from a first electrical circuit (microwave energy source VRF) to a second electrical circuit (electrical load 120) without direct electrical contact, such as, for example, by inductive coupling, capacitive coupling or antenna to antenna energy transfer (wireless).

Figure 2B:
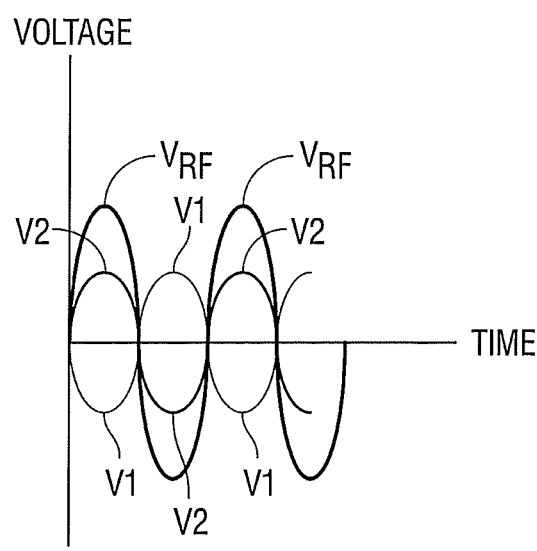
FIG. 2B is a plot of electrical waveforms, from a conventional microwave energy delivery circuit, at various points of the simplified electrical schematic of FIG. 2A.

FIG. 2B is a plot of electrical waveforms at various points in the simplified electrical schematic of FIG. 2A. The microwave generator generates the signal VRF that is applied to the primary side "P" of the generator isolation device 130 with general characteristics of a peak-to-peak amplitude, a phase and a fundamental frequency. VRF is referenced to ground "G" and is transformed across the generator isolation device 130 to the secondary side "S" of the generator isolation device 130 thereby creating a signal at "V1" and "V2" of the second electrical circuit. V1 and V2 have the same fundamental frequency of VRF and related by the formula:

$$VRF=(V1-V2)/ID_{Eff}$$

wherein the constant "ID"$_{Eff}$ accounts for system losses in the circuit 20. The peak-to-peak amplitude of each of V1 and V2 is about half the peak-to-peak amplitude of VRF.

An ungrounded coaxial transmission cable 130 attached to the secondary S of the isolation device 130 carries half of the voltage on the inner conductor 122 and half of the voltage on the outer sheath 124, as illustrated in FIGS. 2A and 2B. This voltage signal V2 applied to the outer sheath 124 may cause energy to radiate from the coaxial transmission cable 120 thereby producing unwanted and excess radiation. In addition, carrying this signal V2 on the outer sheath 124 may result in the generation of standing waves and the generation of unwanted harmonics of the fundamental frequency. As such, the microwave generator 100, the transmission path 125 or the microwave energy delivery device 110 of FIG. 1 may fail radiating limits set by the FCC and may also result in undesirable heating of material or tissue in contact with the outer sheath 124.

Figure 3A:
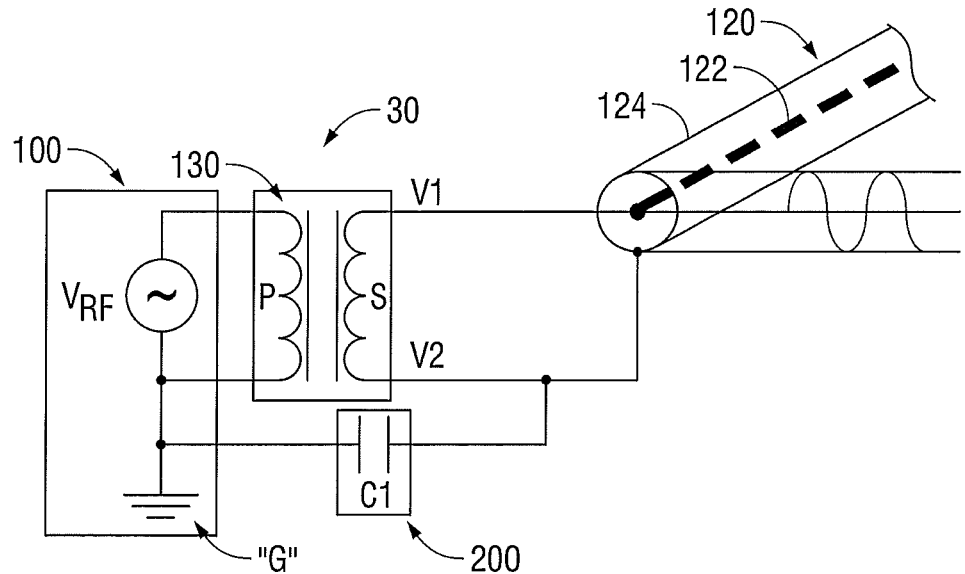
FIG. 3A is a simplified electrical schematic of a microwave energy delivery circuit including an isolation apparatus of the present disclosure.

FIG. 3A is an electrical schematic of a microwave energy delivery circuit 30 with an isolation apparatus 200 according to one embodiment of the present disclosure. The circuit includes a microwave energy source VRF, a generator isolation device 130 (i.e., a transformer), and an electrical load 120 (i.e., a coaxial transmission cable 120 connected to a microwave energy delivery device (not shown)) and an isolation apparatus 200. Isolation apparatus 200 includes a circuit exhibiting the properties of the present disclosure as described herewithin and is illustrated in the schematic as "C1". The capacitance values and properties of the circuit C1 in the isolation apparatus 200 is sufficiently sized such that the circuit C1 has a low impedance at the fundamental frequency of the microwave generator 100 and a high impedance at low frequencies.

Figure 3B:
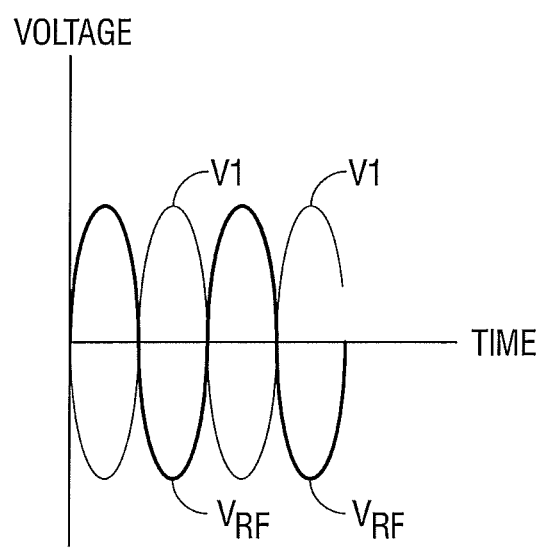
FIG. 3B is a plot of electrical waveforms at various points of the simplified electrical schematic of FIG. 3A.

With the isolation apparatus 200 in the circuit 30, the secondary side S at V2 at the fundamental frequency is capacitive coupled to ground G. FIG. 3B is a plot of the electrical waveforms at VRF and V1. V2 is at ground potential G and is therefore not illustrated in FIG. 3B. V1 is 180° out of phase relative to VRF and the magnitude is related by the formula:

$$VRF = V1/ID_{\mathit{Eff}}$$

wherein the constant "ID"$_{\mathit{Eff}}$ accounts for system losses in the circuit 30. As such, the peak-to-peak amplitude of each of V1 is approximately equal to the peak-to-peak amplitude of VRF and the majority of the microwave signal is carried on the inner conductor 122 of the coaxial transmission cable 120.

The isolation apparatus 200 provides an AC reference point to ground potential for the coaxial outer sheath 124 thus reducing the radiated signal of the coaxial transmission cable. V2 is capacitively coupled to ground potential G and the voltage at V2 is substantially zero.

Figure 4:
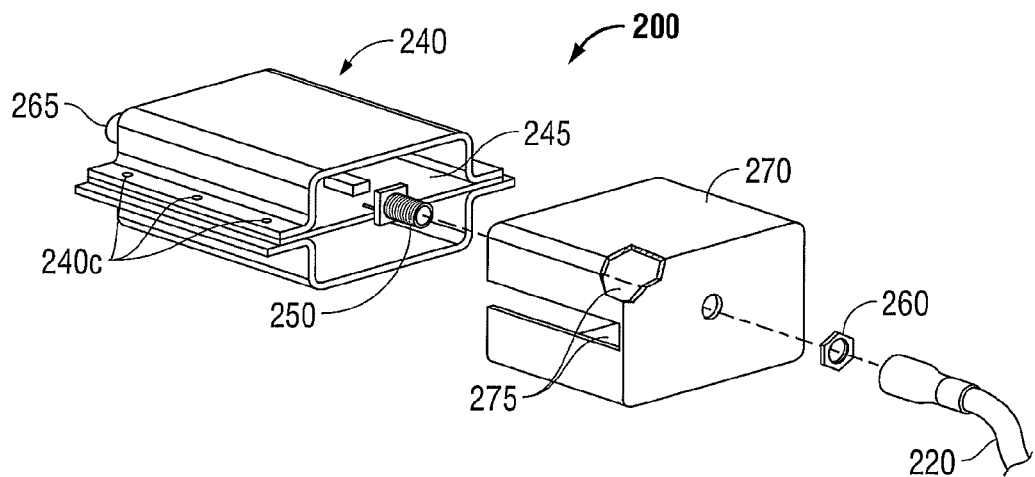
FIG. 4 is a perspective view of an isolation apparatus according to an embodiment of the present disclosure.
Figure 5:
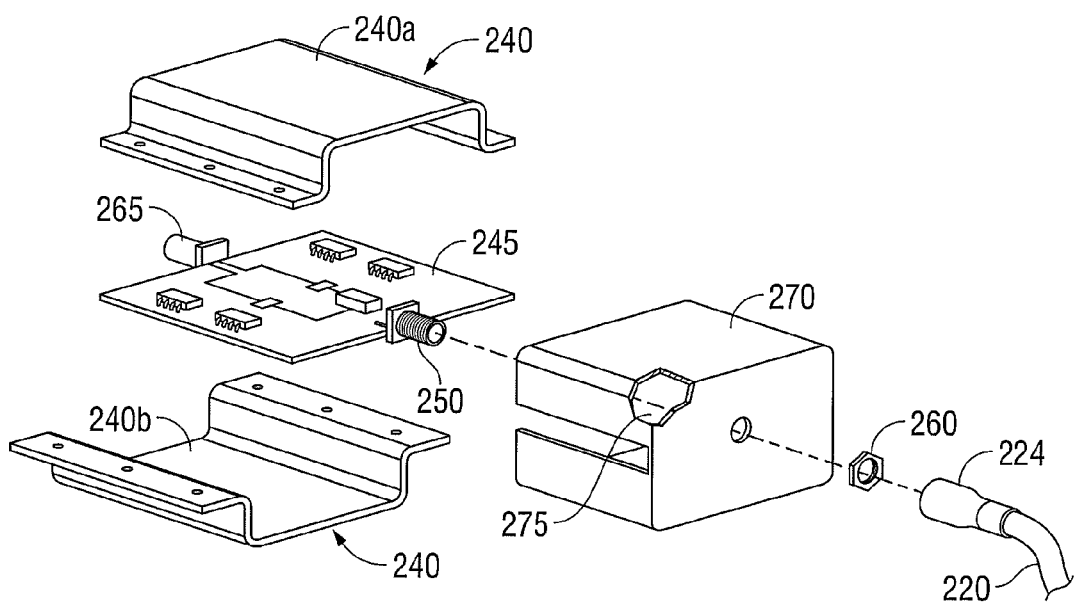
FIG. 5 is an exploded view of the isolation apparatus of FIG. 4.

FIGS. 4 and 5 are perspective views of an isolation apparatus 200 according to an embodiment of the present disclosure. Isolation apparatus 200 includes a ground reference shield 240, an isolation apparatus circuit board 245, a shield connector 250, a generator side connector 265 and a patient reference shield 270.

Ground reference shield 240 may include an upper shield 240a and a lower shield 240b connected at one or more positions. Upper and lower shields 240a, 240b may be formed of a suitable conductive material capable of forming a capacitive relationship with the patient reference shield 270. The capacitive relationship between the ground reference shield 240 and the patient reference shield 270 is described in more detail hereinbelow.

Upper and lower shields 240a, 240b may be connected by one or more mechanical connectors 240c, such as, for example, pins, rivets, fasteners, screws or bolts, or by a suitable connection, such as, for example, a compression connection a hinge connection, a welded or press fit connection. Alternatively, upper and lower shields 240a, 240b may have a combination of connection means, such as, for example, a hinge connection on a side and a locking mechanism or connector on a second side. Any suitable assembly may be used provided the ground reference shield 240 and the patient reference shield 270 form a desirable capacitive relationship therebetween.

Upper and lower shields 240a, 240b are in electrical communication with each other. As illustrated in FIG. 4, mechanical connection 240c may provide a suitable electrical connection between the upper and lower shields 240a, 240b. In another embodiment, upper and lower shields 240a, 240b may be electrically connected via the generator side connector 265.

Patient reference shield 270 is connected to the shield connector 250 by a suitable connector, such as, for example, a threaded shield connector attachment nut 260. Any other suitable connection may be used, such as, for example, a press-fit connection, a slot-fit connection, a locking connection or a welded connection.

Patient reference shield 270, shield connector 250 and the outer sheath 224 of the coaxial transmission cable 220 are in electrical communication with each other. Attachment nut 260 may provide a suitable connection between the patient reference shield 270 and the shield connector 250. Outer sheath 224 of the coaxial transmission cable 220 may connect to the shield connector 250 by a suitable connection, such as, for example, a threaded connection or a press-slip connection. Any other suitable connection may be used provided that it provides suitable electrical contact between the shield connector 250, the patient reference shield 270 and the outer sheath 224.

Patient reference shield 270 is configured to at least partially surround at least a portion of the ground reference shield 240 forming a capacitance gap there between. Gap may be controlled by the thickness of an isolation barrier 275 positioned between the patient reference shield 270 and the ground reference shield 240.

Isolation barrier 275 may be configured as a layer (or laminate) placed adjacent to or formed on one or more surfaces of the patient reference shield 270 and/or the ground reference shield 240. For example, the isolation barrier 275 may be a dielectric paper, such as a dielectric paper sold by DuPont under the trademark NOMEX®. Dielectric paper may be applied to or positioned adjacent the inner surface of the patient reference shield 270 prior to or during assembly. After assembly, the dielectric paper provides a minimum separation or spacing between the inner surface of the patient reference shield 270 and the outer surface of the ground reference shield 240.

Isolation barrier 275 may be a laminate such as, for example an organic-ceramic laminate sold by TACONIC under the product line of RF-35 High Performance Laminates. RF-35 provides suitable peel strength, low moisture absorption and a low dissipation factor thereby minimizing phase shift with frequency. RF-35 may include woven fabric and ceramics and may be coated on one or more surfaces of the isolation apparatus.

In yet another embodiment the isolation barrier 275 may be air. A separation distance between the inner surface of the patient reference shield 270 and the outer surface of the ground reference shield 240 may be maintained by a plurality of insulating offsets (not shown) that provide a desirable separation distance.

The various properties of the isolation apparatus 200 depend on the conductive relationship between the patient reference shield 270 and the ground reference shield 240. The patient reference shield 270 and the ground reference shield 240, separated by a minimal separation distance, form a parallel plate capacitor wherein the capacitance is proportional to the area of opposing shield 240, 270 surfaces and the permeability of the isolation barrier 275 and inversely proportional to the distance between the shields 240, 270.

The capacitance of a parallel-plate capacitor is equal to:

$$\text{Capacitance} = (\in \times A)/d$$

wherein "∈" is the permittivity of the isolation barrier 275, "A" is the area of the opposing shields 240, 270 and "d" is the spacing between the shields 240, 270.

As such, a desired capacitance may be obtained by varying one or more of the area of overlapping surfaces, the dielectric properties of the isolation barrier 275, and the gap between the two opposing shields 240, 270.

In yet another embodiment of the present disclosure the capacitance of the isolation apparatus 200 may be adjustable. In one embodiment, a gap adjustment mechanism (not shown) may vary the position of the ground reference shield 240 relative to the patient reference shield 270 thereby increasing or decreasing the gap therebetween. Gap adjustment mechanism (not shown) may change the gap dynamically or manually. A dynamic adjustment may be necessary if the microwave generator varies the fundamental frequency during energy delivery. A manual adjustment may be used to calibrate the isolation apparatus 200 during assembly.

Capacitance of the isolation apparatus 200 may be adjusted by varying the overlap between the ground reference shield 240 and the patient reference shield 270. Overlap adjustment mechanism (not shown) may reposition the shields 240, 270 relative to each other either dynamically or manually.

Capacitance of the isolation apparatus 200 may be adjusted by changing the dielectric properties of the isolation barrier 275 or by changing the type of material used for the isolation barrier.

Isolation circuit board 245 is housed within the ground reference shield 240 of the isolation apparatus 200. Isolation circuit board 245 may include a circuit configured to provide isolation between a microwave generator (not shown) and a coaxial transmission cable 220, as discussed hereinabove.

Figure 6:
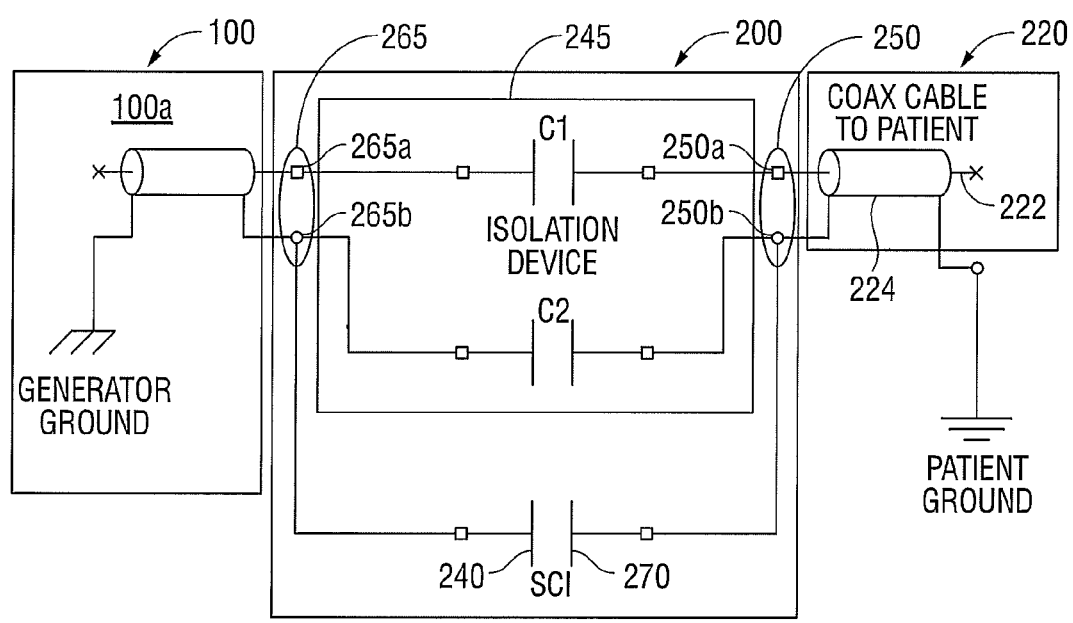
FIG. 6 is an electrical schematic of the isolation apparatus of FIG. 4 in a microwave energy delivery circuit.

FIG. 6 is an electrical schematic of the isolation apparatus of FIG. 4 and the microwave energy delivery system of FIG. 1. The adjacent surfaces of the ground reference shield 240, connected to the generator side connector 265, and the patient reference shield 270, connected to the coaxial sheath 224, form the shield coupling capacitor "SC1". Isolation circuit board 245 includes first and second isolation capacitors "C1" and "C2", respectively, that provide electrical isolation, as discussed herein above, between the microwave generator 100 and the coaxial transmission cable 220.

In use, a microwave signal is supplied to the generator side connector 265. The inner conductor 265a of the microwave generator connector 265 connects to the first isolation capacitor C1. The outer conductor 265b of the microwave generator connector 265 connects to the second isolation capacitor C2 and to the ground reference shield 240 of the shield coupling capacitor SC1. At the fundamental frequency of the microwave energy delivery system the first and second isolation capacitor C1, C2 appear as short circuits and pass the signal at the fundamental frequency to the inner conductor 250a and the outer conductor 250b, respectively, of the shield connector 250 and to the inner conductor 222 and the outer sheath 224 of the coaxial transmission cable 220. The patient reference shield 270, connected to the outer sheath 224 of the coaxial transmission cable, and the ground reference shield 240 form the shield coupling capacitor SC1 thereby providing a ground reference for the coaxial transmission cable 220.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A system for reducing radiated emissions, the system comprising:
    a microwave generator that supplies microwave energy at a fundamental frequency;
    a coaxial transmission cable that transmits microwave energy between the microwave generator and a microwave energy delivery device; and
    an isolation apparatus connected between the microwave generator and the coaxial transmission cable, the isolation apparatus configured to electrically isolate the coaxial transmission cable from the microwave generator, the isolation apparatus including:
        an isolation circuit board configured to electrically isolate the microwave generator and the coaxial transmission cable while passing microwave energy therebetween;
        a ground reference shield connected to a microwave generator ground reference and configured to house the isolation circuit board; and
        a patient reference shield at least partially surrounding the ground reference shield and forming a capacitive relationship therebetween, the ground reference shield and the patient reference shield forming a capacitor that capacitively couples the microwave generator ground reference to the coaxial transmission cable;
    wherein the isolation apparatus capacitively couples the microwave generator ground reference to the coaxial transmission cable.

2. The system according to claim 1, wherein the isolation apparatus further includes an isolation barrier disposed between the ground reference shield and the patient reference shield.

3. The system according to claim 1, wherein the ground reference shield includes:
    an upper shield; and
    a lower shield in electrical communication with the upper shield.

4. The system according to claim 3, wherein the isolation circuit board is disposed between the upper shield and the lower shield.

5. The system according to claim 3, wherein the isolation apparatus further includes a generator side connector connected to the upper shield and the lower shield.

6. The system according to claim 5, wherein the generator side connector includes an inner conductor and an outer conductor.

7. The system according to claim 6, wherein the isolation circuit board includes a first isolation capacitor connected to the inner conductor of the generator side connector and a second isolation capacitor connected to the outer conductor of the generator side connector.

8. The system according to claim 1, wherein the isolation apparatus further includes a shield connector coupled to the patient reference shield.

9. The system according to claim 8, wherein the coaxial transmission cable includes an outer sheath coupled to the shield connector.

* * * * *